(12) United States Patent
Berman et al.

(10) Patent No.: US 7,068,753 B2
(45) Date of Patent: Jun. 27, 2006

(54) ENHANCEMENT OF X-RAY REFLECTOMETRY BY MEASUREMENT OF DIFFUSE REFLECTIONS

(75) Inventors: David Berman, Kiryat Tivon (IL); Isaac Mazor, Haifa (IL); Boris Yokhin, Nazareth Illit (IL); Amos Gvirtzman, Moshav Zippori (IL)

(73) Assignee: Jordan Valley Applied Radiation Ltd., Migdal Ha'Emek (IL)

( * ) Notice: Subject to any disclaimer, the term of this patent is extended or adjusted under 35 U.S.C. 154(b) by 71 days.

(21) Appl. No.: 10/902,177

(22) Filed: Jul. 30, 2004

(65) Prior Publication Data

US 2006/0023836 A1    Feb. 2, 2006

(51) Int. Cl.
*G01N 23/20* (2006.01)

(52) U.S. Cl. .......................................... 378/70; 378/89
(58) Field of Classification Search ............ 378/70–90; 356/237.2–237.5
See application file for complete search history.

(56) References Cited

U.S. PATENT DOCUMENTS

| | | | |
|---|---|---|---|
| 3,980,568 A | 9/1976 | Pitchford et al. .......... 250/276 |
| 4,525,853 A | 6/1985 | Keem et al. .................. 378/84 |
| 4,715,718 A * | 12/1987 | Evans .......................... 356/446 |
| 4,725,963 A | 2/1988 | Taylor et al. ................ 364/507 |
| 4,916,720 A | 4/1990 | Yamamoto et al. .......... 378/81 |
| 4,949,367 A | 8/1990 | Huizing et al. .............. 378/84 |
| 4,989,226 A | 1/1991 | Woodbury et al. ......... 378/145 |
| 5,151,588 A | 9/1992 | Kiri et al. ................. 250/208.1 |
| 5,570,408 A | 10/1996 | Gibson ....................... 378/145 |
| 5,574,284 A | 11/1996 | Farr ...................... 250/370.06 |
| 5,619,548 A | 4/1997 | Koppel ........................ 378/70 |
| 5,740,226 A | 4/1998 | Komiya et al. .............. 378/70 |
| 5,798,525 A | 8/1998 | Benizri-Carl et al. ....... 250/310 |
| 5,937,026 A | 8/1999 | Satoh ........................... 378/44 |
| 5,949,847 A | 9/1999 | Terada et al. ................. 378/90 |
| 5,963,329 A | 10/1999 | Conrad et al. .............. 356/372 |
| 6,041,098 A | 3/2000 | Touryanski et al. .......... 378/70 |
| 6,192,103 B1 | 2/2001 | Wormington et al. ......... 378/73 |
| 6,226,347 B1 | 5/2001 | Golenhofen ................. 378/45 |
| 6,226,349 B1 | 5/2001 | Schuster et al. .............. 378/84 |
| 6,381,303 B1 | 4/2002 | Vu et al. ...................... 378/46 |
| 6,389,102 B1 | 5/2002 | Mazor et al. ................. 378/89 |
| 6,393,093 B1 | 5/2002 | Jans et al. .................... 378/45 |

(Continued)

FOREIGN PATENT DOCUMENTS

JP            5-322804        12/1993

(Continued)

OTHER PUBLICATIONS

Wiener et al., "Characterization of Titanium Nitride Layers by Grazing-Emission X-Ray Fluorescence Spectrometry", in Applied Surface Science 125 (1998), p. 129.

Hayashi et al., "Refracted X-Rays Propagating Near the Surface under Grazing Incidence Condition", Spectrochimica Acta, Part B 54, 1999, pp. 227-230.

(Continued)

*Primary Examiner*—Edward J. Glick
*Assistant Examiner*—Jurie Yun
(74) *Attorney, Agent, or Firm*—Smith, Gambrell & Russell (57) ABSTRACT

A method for inspection of a sample having a surface layer. The method includes acquiring a first reflectance spectrum of the sample while irradiating the sample with a collimated beam of X-rays, and processing the first reflectance spectrum to measure a diffuse reflection property of the sample. A second reflectance spectrum of the sample is acquired while irradiating the sample with a converging beam of the X-rays. The second reflectance spectrum is analyzed using the diffuse reflection property so as to determine a characteristic of the surface layer of the sample.

21 Claims, 6 Drawing Sheets

U.S. PATENT DOCUMENTS

| | | | |
|---|---|---|---|
| 6,453,006 B1 | 9/2002 | Koppel et al. | 378/86 |
| 6,507,634 B1 | 1/2003 | Koppel et al. | 378/54 |
| 6,512,814 B1 | 1/2003 | Yokhin et al. | 378/82 |
| 6,556,652 B1 | 4/2003 | Mazor et al. | 378/86 |
| 6,639,968 B1 | 10/2003 | Yokhin et al. | 378/70 |
| 6,643,354 B1 | 11/2003 | Koppel et al. | 378/86 |
| 6,680,996 B1 | 1/2004 | Yokhin et al. | 378/70 |
| 6,711,232 B1 | 3/2004 | Janik | 378/70 |
| 6,744,950 B1 | 6/2004 | Aleksoff | 385/48 |
| 6,750,952 B1 | 6/2004 | Grodnensky et al. | 355/77 |
| 6,771,735 B1 | 8/2004 | Janik et al. | 378/70 |
| 6,810,105 B1 | 10/2004 | Nasser-Ghodsi et al. | 378/44 |
| 2001/0028699 A1 | 10/2001 | Iwasaki | 378/84 |
| 2001/0043668 A1 | 11/2001 | Hayashi et al. | 378/89 |
| 2002/0097837 A1 | 7/2002 | Fanton et al. | 378/82 |
| 2002/0110218 A1 | 8/2002 | Koppel et al. | 378/86 |
| 2003/0157559 A1 | 8/2003 | Omote et al. | 437/7.1 |
| 2004/0052330 A1 | 3/2004 | Koppel et al. | 378/46 |
| 2004/0156474 A1 | 8/2004 | Yokhin et al. | 378/70 |
| 2004/0218707 A1 | 11/2004 | Koppel et al. | 378/70 |

FOREIGN PATENT DOCUMENTS

| | | |
|---|---|---|
| JP | 9-308339 | 11/1997 |
| JP | 11-14561 | 1/1999 |

OTHER PUBLICATIONS

Series 5000 Model XTF5011 X-Ray Tube Information, Oxford Instruments Inc., Scotts Valley, GA, U.S.A., Jun. 1998.

Monolithic Polycapillary Lens Information, X-Ray Optical Systems, Inc., Albany, NY, U.S.A., Dec. 29, 1998. (web site: www.xos.com).

Hugues Guerault, "Specular reflectivity and off-specular scattering", Tools for roughness investigation, Dec. 2000.

Jones, et al., "Small angle x-ray scattering for sub-100 nm pattern characterization", Applied Physics Letters 83:19 (2003), pp. 4059-4061.

Hu et al., "Small angle x-ray scattering metrology for sidewall angle and cross section of nanometer scale line gratings", Journal of Applied Physics 96:4 (2004), pp. 1983-1987.

Wu et al., "Small angle neutron scattering measurements of nanoscale lithographic features", Journal of Applied Physics 88:12 (2000), pp. 7298-7303.

Kojima, et al., "Structural characterization of thin films by x-ray reflectivity", Rigaku Journal 16:2 (1999), pp. 31-41.

Stommer, "X-ray scattering from silicon surfaces", in Semiconductor International (May 1, 1998).

Yoneda, "Anomalous surface reflection of X Rays", Physical Review 131, pp. 2010-2013, 1963.

Stommer, et al., "Characterization of semiconductor materials by X-ray scattering", Electrochemical Society Proceedings vol. 99-16, pp. 117-133, 1999.

Bowen, et al., "X-Ray metrology by diffraction and reflectivity", Characterization and Metrology for ULSI Technology, 2000 International Conference (American Institute of Physics, 2001).

Ulyanekov, "Introduction to high resolution X-Ray diffraction", Workshop on X-ray characterization of thin layers (Uckley, May 21-23, 2003).

Ito, "X-ray Scattering Method for Determining Pore-Size Distribution in Low-k Thin Films", Presented at the International Sematech Ultra-Low-k Workshop (San Francisco, CA, Jun. 6-7, 2002).

Naudon, et al., "New apparatus for grazing X-ray reflectometry in the angle-resoived dispresive mode", J. Appl. Cryst. 1989, vol. 22, pp. 46-464.

N. Wu, et al, "Substepping and its Application to HST Imaging", Jul. 28, 2003.

Wormington, Characterization of Pore Size Distribution in Low k Dielectrics Using X-ray Reflectivity, presented at the Sematech Gate Stack Engineering Workshop (Austin, Texas, May 2, 2002).

J. Spear, "Metrology for low-k materials", Silknet Aliance, 2003.

J.R. Levine Parrill, et al, "GISAXS—Glancing Incidence Small Angle X-ray Scattering", Journal de Physique IV 3 (Dec. 1993), pp. 411-417.

Jaklevic, et al., "High Rate X-Ray Fluorescence Analysis by Pulsed Excitation", IEEE Transactions on Nuclear Science NS-19:3 (1972), pp. 392-395.

Jaklevic, et al., "Small X-Ray Tubes for Energy Dispersive Analysis Using Semiconductor Spectrometers", Advances in X-Ray Analysis 15 (1972), pp. 266-275.

Jaklevic, et al., "Energy Dispersive X-Ray Fluorescence Spectrometry Using Pulsed X-Ray Excitation", Advances in X-Ray Analysis 19 (1976).

Jaklevic, et al., "Energy Dispersive X-Ray Fluorescence Spectrometry Using Pulsed X-Ray Excitation", Advances in X-Ray Analysis 19 (1976).

T.C. Huang, et al., "Characterization of single-and multiple-layer films by X-Ray reflectrometry", Advances in X-Ray analysis, vol. 35, Pleneum Press, New York, 1992.

J. Miyahara, et al., "A new type of X-ray area detector utilizing laser stimulated luminescence", Nuclear Instruments and Methods in Physics Research A246 (1986) 572-578.

P.B. Kenway, et al., "X-Ray Optics and Microanalysis 1992", Proceedings of the Thirteenth International Congresss, UMIST, UK, Aug. 31-Sep. 4, 1992.

D.H. Lumb, et al., "Performance of CCDs for X-Ray Imaging and Spectometry", Nuclear instruments and methods in physics research 221 (1984), 150-158.

E.P. Bertin, "Principles and Practice of X-Ray Spectometric Analysis", Plenum Press, New-York-London, 1975.

A.G. Michette, et al., "X-Ray Science and Technology", Institute of Physics, Bristol and Philadelphia, 1993.

G.S. Knapp, et al., "Synchrotron and Laboratory Studies Utilizing a New Powder Diffractiion Technique", Advances in X-Ray Analysis, vol. 36, Plenum Press, New York, 1993.

K.L. Smith, et al., "Use of two-dimensional, position sensitive detector for collecting pole figures", Advances in X-Ray Analysis, vol. 36, Plenum Press, New York, 1993.

B.B. He, et al., "Advantages of using 2D detectors for residual stress measurements", Advances in X-Ray Analysis, vol. 42, 2000.

S.N. Sulyanov, et al., "Using a two-dimensional detector for X-ray powder diffractometry", J. Appl. Cryst. (1994) 27, 934-942.

F.D. Finkelstein, et al., "On the collection of diffraction data simultaneously over a range of energy", Nuclear Instruments and Methods in Physics Research A 347 (1994) 495-498.

A. Longoni, et al., "A new XRF spectrometer based on a ring-shaped multi-element silicon drift detector and on X-ray capillary optics", 2002.

A.D. Dane, "Application of generic algorithms for characterization of thin layered materials by glancing incidence X-ray reflectometry", Physica B 253 (1998), 254-268.

S. DiFonzo et al. "Non-destructive determination of local strain with 100-nanometre spatial resolution" Nature vol. 403, Feb. 10, 200 pp. 638-640.

* cited by examiner

ENHANCEMENT OF X-RAY REFLECTOMETRY BY MEASUREMENT OF DIFFUSE REFLECTIONS

FIELD OF THE INVENTION

The present invention relates generally to analytical instruments, and specifically to instruments and methods for thin film analysis using X-rays.

BACKGROUND OF THE INVENTION

X-ray reflectometry (XRR) is a well-known technique for measuring the thickness, density and surface quality of thin film layers deposited on a substrate. Conventional X-ray reflectometers are sold by a number of companies, among them Technos (Osaka, Japan), Siemens (Munich, Germany) and Bede Scientific Instrument (Durham, UK). Such reflectometers typically operate by irradiating a sample with a beam of X-rays at grazing incidence, i.e., at a small angle relative to the surface of the sample, near the total external reflection angle of the sample material. Measurement of X-ray intensity reflected from the sample as a function of angle gives a pattern of interference fringes, which is analyzed to determine the properties of the film layers responsible for creating the fringe pattern.

A method for analyzing the X-ray data to determine film thickness is described, for example, in U.S. Pat. No. 5,740,226, to Komiya et al., whose disclosure is incorporated herein by reference. After measuring X-ray reflectance as a function of angle, an average reflectance curve is fitted to the fringe spectrum. The average curve is based on a formula that expresses attenuation, background and surface roughness of the film. The fitted average reflectance curve is then used in extracting the oscillatory component of the fringe spectrum. This component is Fourier transformed to find the film thickness.

U.S. Pat. No. 5,619,548, to Koppel, whose disclosure is incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, density and surface roughness.

U.S. Pat. No. 5,923,720, to Barton et al., whose disclosure is incorporated herein by reference, also describes an X-ray spectrometer based on a curved crystal monochromator. The monochromator has the shape of a tapered logarithmic spiral, which is described as achieving a finer focal spot on a sample surface than prior art monochromators. X-rays reflected or diffracted from the sample surface are received by a position-sensitive detector.

U.S. Pat. Nos. 6,512,814 and 6,639,968, to Yokhin et al., whose disclosures are incorporated herein by reference, describe an X-ray reflectometry system that includes a dynamic shutter, which is adjustably positionable to intercept the X-rays incident on the sample. This shutter, along with other features of the system, permits detection of XRR fringe patterns with high dynamic range. These patents also disclose improved methods for analysis of the XRR fringe pattern in order to determine thin film properties, including density, thickness and surface roughness. The high dynamic range enables the system to determine these properties accurately not only for the upper thin film layer, but also for one or more underlying layers on the surface of the sample.

Another common method of X-ray reflectometric measurement is described, for example, in an article by Naudon et al., entitled "New Apparatus for Grazing X-ray Reflectometry in the Angle-Resolved Dispersive Mode," in *Journal of Applied Crystallography* 22 (1989), p. 460, which is incorporated herein by reference. A divergent beam of X-rays is directed toward the surface of a sample at grazing incidence, and a detector opposite the X-ray beam source collects reflected X-rays. A knife edge is placed close to the sample surface immediately above a measurement location in order to cut off the primary X-ray beam. A monochromator between the sample and the detector (rather than between the source and sample, as in U.S. Pat. No. 5,619,548) selects the wavelength of the reflected X-ray beam that is to reach the detector.

XRR may also be used in situ, within a deposition furnace, to inspect thin film layers in production on a semiconductor wafer, as described, for example, by Hayashi et al., in U.S. Patent Application Publication U.S. 2001/0043668 A1, whose disclosure is incorporated herein by reference. The furnace is provided with X-ray incidence and extraction windows in its side walls. The substrate upon which the thin film has been deposited is irradiated through the incidence window, and the X-rays reflected from the substrate are sensed through the X-ray extraction window.

Whereas the references cited above are directed to measurement of specular X-ray reflections, diffuse X-ray reflections (alternatively referred to as diffuse scattering) can also provide surface information. Measurement of diffuse X-ray scattering is described, for example, by Stömmer in "X-ray Scattering from Silicon Surfaces," in *Semiconductor International* (May 1, 1998), which is incorporated herein by reference. This article describes an experimental set-up in which a sample is irradiated by a collimated X-ray source, and scattered X-rays from the sample are received by a detector. The detector is positioned so that the sum of the angles of incidence and scattering is fixed at a total angle, which is denoted $2\Theta$. The sample is mounted on a goniometer, which permits the tilt angle of the sample (denoted $\Omega$) to be varied relative to the incident beam, without changing the total angle $2\Theta$.

In this arrangement, the scattered X-ray signal received by the detector is measured as a function of the tilt angle $\Omega$. A sharp specular peak is observed at $\Omega=\Theta$. Additional, diffuse reflection peaks are observed on both sides of the specular peak, at angles $\Omega=\Phi_c$ and $\Omega=2\Theta-\Phi_c$, wherein $\Phi_c$ is the critical angle for total external reflection from the sample. These diffuse reflection peaks were first observed by Yoneda, who described his findings in an article entitled "Anomalous Surface Reflection of X Rays," *Physical Review* 131, pages 2010–2013 (1963), which is incorporated herein by reference. The peaks are therefore commonly referred to as "Yoneda wings." As noted by Stömmer, the shape of the diffuse scattering curve is determined, inter alia, by the surface roughness of the sample, and the diffuse scattering measurements can be analyzed to determine surface properties.

SUMMARY OF THE INVENTION

In embodiments of the present invention, specular and diffuse XRR spectra are combined in order to provide richer, more accurate information regarding one or more surface layers of a sample. In some embodiments, these measurements are acquired using a dual-purpose XRR system, which includes an X-ray source that may be configured to irradiate a sample with either a converging beam or a collimated beam. A detector, typically a detector array, detects the X-rays reflected from the sample over a range of angles. (As noted above, the terms "reflected," "reflection" and "reflectance" are used in the present patent application and in the claims to refer to both specular and diffuse reflection, which is also known in the art as diffuse scattering.)

In the collimated-beam configuration, the system acquires a first reflectance spectrum that includes diffuse reflectance information. Typically, this spectrum is processed to determine the location and amplitude of at least one of the Yoneda peaks, which are indicative of the critical angle and surface roughness of the sample.

In the converging-beam configuration, the system acquires a second reflectance spectrum, in which specular reflection dominates. The shape of this spectrum is analyzed, typically by fitting the spectrum to a theoretical model, in order to determine characteristics of one or more surface layers of the sample. These characteristics may include, for example, the thickness, density and/or surface roughness of thin film layers at the surface of a semiconductor wafer. Depending on the roughness of the surface, however, the specular reflectance spectrum may still contain substantial background due to diffuse reflections, which can reduce the quality of the fit. Therefore, prior to performing the fit, the second reflectance spectrum may be corrected to remove the diffuse reflection background, based on the measurement of diffuse reflectance in the first spectrum. Furthermore, the critical angle and/or surface roughness that were obtained from the first reflectance spectrum may be used as parameters in the fit, in order to enhance the accuracy of estimation of the surface layer characteristics.

Although the embodiments of the present invention described herein are directly mainly toward enhancing X-ray measurements on thin films, and particularly on films formed on semiconductor wafers, the principles of the present invention can similarly be used in other applications of X-ray reflectometry and scattering, as well as in other types of radiation-based analysis.

There is therefore provided, in accordance with an embodiment of the present invention, a method for inspection of a sample having a surface layer, the method including:

acquiring a first reflectance spectrum of the sample while irradiating the sample with a collimated beam of X-rays;

processing the first reflectance spectrum to measure a diffuse reflection property of the sample;

acquiring a second reflectance spectrum of the sample while irradiating the sample with a converging beam of the X-rays; and analyzing the second reflectance spectrum using the diffuse reflection property so as to determine a characteristic of the surface layer of the sample.

In a disclosed embodiment, acquiring the first reflectance spectrum includes introducing a slit into the converging beam so as to collimate the beam.

In some embodiments, acquiring the first reflectance spectrum includes irradiating the sample with the collimated beam at a predetermined incidence angle, and receiving the X-rays simultaneously over a range of elevation angles using a detector array. Typically, acquiring the second reflectance spectrum includes receiving the X-rays simultaneously over the range of elevation angles using the detector array that was also used in acquiring the first reflectance spectrum.

In an aspect of the invention, processing the first reflectance spectrum includes detecting a Yoneda wing in the first reflectance spectrum. Typically, detecting the Yoneda wing includes determining a critical angle for total external reflection from the sample responsively to an angular location of the Yoneda wing. Additionally or alternatively, detecting the Yoneda wing includes determining a measure of roughness of the surface layer responsively to an amplitude of the Yoneda wing.

In some embodiments, analyzing the second reflectance spectrum includes estimating a diffuse reflection background responsively to the first reflectance spectrum, and subtracting the diffuse reflection background from the second reflectance spectrum.

Typically, analyzing the second reflectance spectrum includes determining at least one of a density, a thickness and a surface roughness of the surface layer.

In a disclosed embodiment, the sample includes a semiconductor wafer, and analyzing the second reflectance spectrum includes determining a quality of a thin film layer formed on the wafer.

There is also provided, in accordance with an embodiment of the present invention, apparatus for inspection of a sample having a surface layer, the apparatus including:

a radiation source, which is adapted to direct a collimated beam of X-rays toward a surface of the sample in a first configuration of the apparatus, and to direct a converging beam of the X-rays toward the surface of the sample in a second configuration of the apparatus;

a detector assembly, which is arranged to sense the X-rays reflected from the surface so as to generate first and second reflectance spectra as a function of elevation angle relative to the surface in the first and second configurations, respectively; and a signal processor, which is coupled to receive and process the first reflectance spectrum so as to measure a diffuse reflection property of the sample, and to analyze the second reflectance spectrum using the diffuse reflection property so as to determine a characteristic of the surface layer of the sample.

There is additionally provided, in accordance with an embodiment of the present invention, a cluster tool for producing microelectronic devices, including:

a deposition station, which is adapted to deposit a thin-film layer on a surface of a semiconductor wafer; and an inspection station, including:

a radiation source, which is adapted to direct a collimated beam of X-rays toward the surface of the wafer in a first configuration of the inspection station, and to direct a converging beam of the X-rays toward the surface of the wafer in a second configuration of the inspection station;

a detector assembly, which is arranged to sense the X-rays reflected from the surface so as to generate first and second reflectance spectra as a function of elevation angle relative to the surface in the first and second configurations, respectively; and a signal processor, which is coupled to receive and process the first reflectance spectrum so as to measure a diffuse reflection property of the surface, and to analyze the second reflectance spectrum using the diffuse reflection property so as to determine a characteristic of the thin-film layer.

There is further provided, in accordance with an embodiment of the present invention, apparatus for producing microelectronic devices, including:

a production chamber, which is adapted to receive a semiconductor wafer;

a deposition device, which is adapted to deposit a thin-film layer on a surface of the semiconductor wafer within the chamber;

a radiation source, which is adapted to direct a collimated beam of X-rays toward the surface of the wafer in the production chamber in a first configuration of the source, and to direct a converging beam of the X-rays toward the surface of the wafer in the production chamber in a second configuration of the source;

a detector assembly, which is arranged to sense the X-rays reflected from the surface of the wafer in the production chamber so as to generate first and second reflectance spectra as a function of elevation angle relative to the surface in the first and second configurations, respectively; and a signal processor, which is coupled to receive and process the first reflectance spectrum so as to measure a diffuse reflection property of the surface, and to analyze the second reflectance spectrum using the diffuse reflection property so as to determine a characteristic of the thin-film layer.

The present invention will be more fully understood from the following detailed description of the embodiments thereof, taken together with the drawings in which:

DETAILED DESCRIPTION OF EMBODIMENTS

Figure 1:
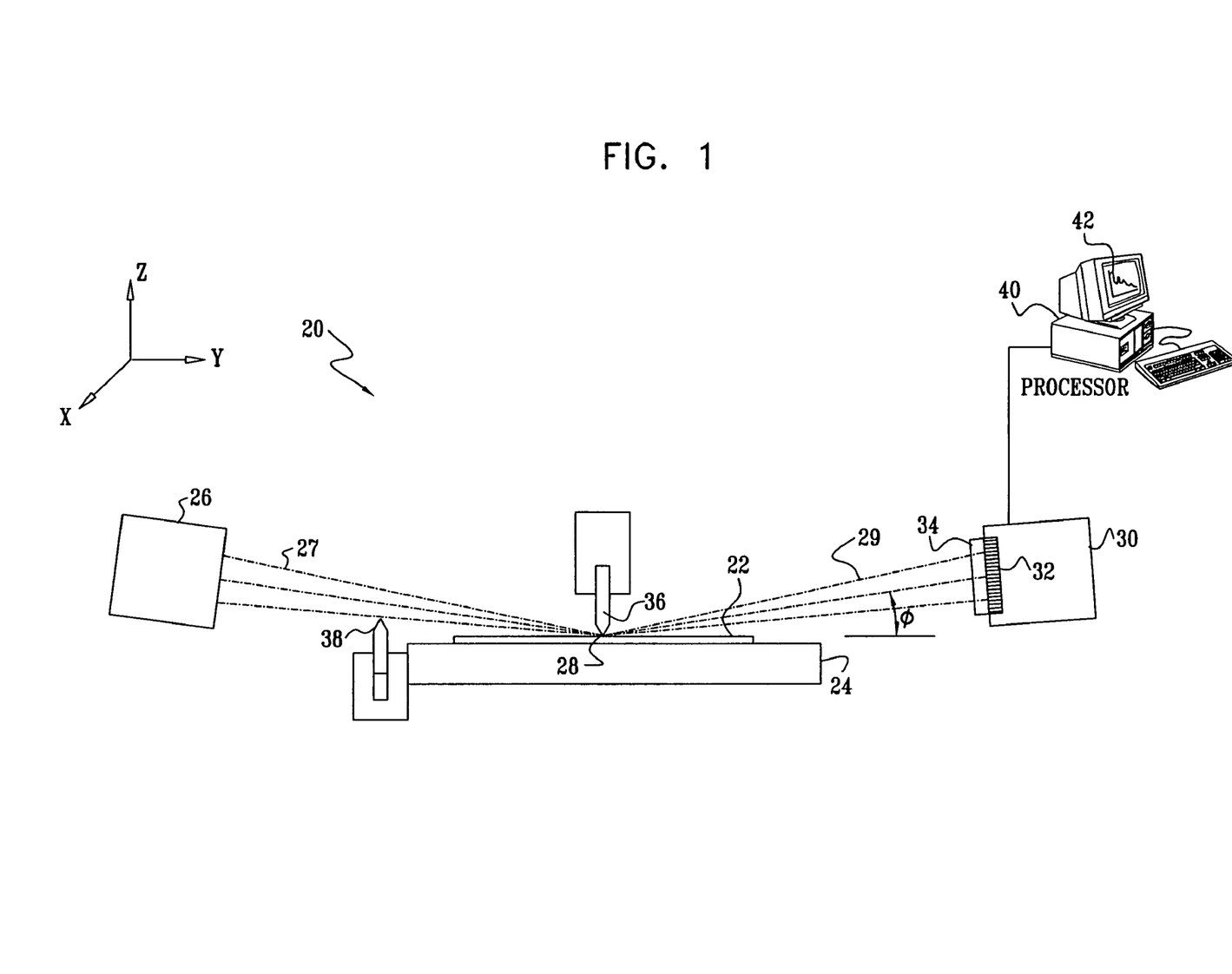
FIG. 1 is a schematic side view of a system for X-ray reflectometry (XRR) measurements in a converging-beam configuration, in accordance with an embodiment of the present invention.
Figure 2:
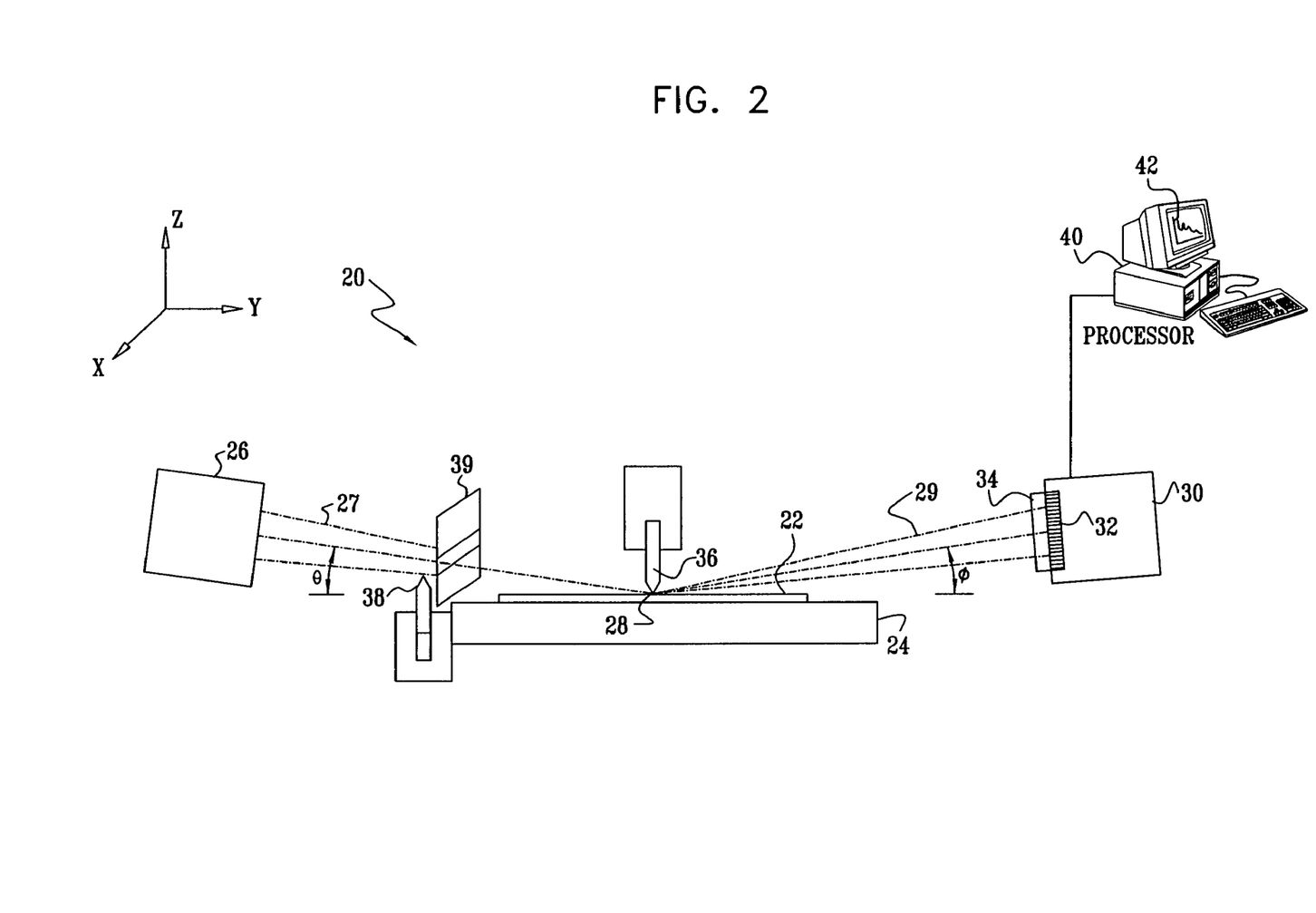
FIG. 2 is a schematic side view of a system for X-ray reflectometry (XRR) measurements in a collimated-beam configuration, in accordance with an embodiment of the present invention.

Reference is now made to FIG. 1, which is a schematic side view of a system 20 for X-ray reflectometry (XRR), in accordance with an embodiment of the present invention. In the configuration shown in this figure, system 20 irradiates a sample 22, such as a semiconductor wafer, with a converging beam 27 of X-rays, for the purpose of measuring specular X-ray reflectance of the sample. System 20 in this configuration is similar to the XRR system described in the above-mentioned U.S. Pat. No. 6,512,814, with the addition of features and capabilities described herein. A second configuration, in which the sample is irradiated with a collimated X-ray beam, is shown in FIG. 2.

Sample 22 is mounted on a motion stage 24, allowing accurate adjustment of the position and orientation of the sample. An X-ray source 26, typically an X-ray tube with suitable monochromatizing optics (not shown), generates converging beam 27, which irradiates a small area 28 on sample 22. For example, the XTF5011 X-ray tube, produced by Oxford Instruments (Scotts Valley, Calif.), may be used as the X-ray source. A typical X-ray energy for reflectometric and scattering measurements in system 20 is about 8.05 keV (CuKal). Alternatively, other energies may be used, such as 5.4 keV (CrKal).

A number of different optical configurations that may be used in source 26 to generate converging beam 27 are described in U.S. Pat. No. 6,381,303, whose disclosure is incorporated herein by reference. For example, the optics may comprise a curved crystal monochromator, such as the Doubly-Bent Focusing Crystal Optic, produced by XOS Inc., of Albany, N.Y. Other suitable optics are described in the above-mentioned U.S. Pat. Nos. 5,619,548 and 5,923,720. The doubly-curved focusing crystal causes beam 27 to converge in both the horizontal (X) and vertical (Z) directions, so as to focus approximately to a point in area 28. Typically, the X-rays converge on area 28 over a range of incident angles from about 0° to 4.5°, although larger or smaller ranges may be used. Alternatively, a cylindrical optic may be used to focus beam 27 so that the beam converges to a line on the sample surface. Further possible optical configurations will be apparent to those skilled in the art.

A dynamic knife edge 36 and shutter 38 may be used to limit the angular extent of incident beam 27 of the X-rays in the vertical direction (i.e., perpendicular to the plane of sample 22). An addition slit (not shown) may be used to limit the beam in the horizontal direction. The use of knife edge 36 and shutter 38 in XRR measurements is described in detail in the above-mentioned U.S. Pat. No. 6,512,814. Briefly, for optimal detection of low-angle reflections, near 0°, shutter 38 is withdrawn outside the extent of incident beam 27, while knife edge 36 is positioned over area 28 and is lowered to reduce the effective vertical cross-section of the beam. As a result, the lateral dimension of the X-ray spot incident on area 28 is reduced.

On the other hand, for effective detection of weaker, high-angle reflections, knife edge 36 is withdrawn from beam 27, while shutter 38 is positioned to cut off the low-angle portion of the beam. Typically, the shutter cuts off incident radiation that is below 0.6° relative to the surface. (Alternatively, the shutter may be positioned to cut off the low-angle portion of reflected beam 29.) In this manner, only the high-angle reflections from sample 22 reach the detector array, and not the strong low-angle reflections, thus enhancing the signal/background ratio of the high-angle measurement.

A reflected beam 29 of X-rays from sample 22 is collected by a detector assembly 30. Typically, assembly 30 collects reflected X-rays over a range of reflection angles in the vertical direction, as a function of elevation angle ($\phi$) between about 0° and 3°, both below and above the critical angle of the sample for total external reflection, $\Phi_c$. (For clarity of illustration, the angles shown in the figures are exaggerated, as is the elevation of source 26 and detector assembly 30 above the plane of sample 22 in FIG. 1.)

Assembly 30 comprises a detector array 32, such as a CCD array, as described in U.S. Pat. No. 6,512,814. Although for simplicity of illustration, only a single row of detectors elements is shown in the figures, with a relatively small number of detector elements, array 32 generally includes a greater number of elements, arranged as either a linear array or a matrix (two-dimensional) array. Assembly 30 further comprises a window 34 made of a suitable X-ray transparent material, such as beryllium, spaced in front of the detector array, between the array and the sample.

A signal processor 40 analyzes the output of assembly 30, so as to determine a distribution 42 of the flux of X-ray photons reflected from sample 22 as a function of angle at a given energy or over a range of energies. Typically, sample 22 has one or more thin surface layers, such as thin films, at area 28, so that distribution 42 as a function of elevation angle exhibits an oscillatory structure due to interference effects among reflected X-ray waves from the interfaces between the layers. Processor 40 analyzes characteristics of the angular distribution in order to determine characteristics of one or more of the surface layers of the sample, such as the thickness, density and surface quality of the layer, using methods of analysis described hereinbelow.

FIG. 2 shows an alternative configuration of system 20, in which sample 22 is irradiated by a collimated beam. This configuration is used for measurement of diffuse X-ray reflectance. Various means may be used to collimate the X-ray beam. In the example shown in FIG. 2, a narrow, horizontal slit 39 is positioned in the incident beam path. Typically, the slit cuts down the convergence angle of the incident beam to about 0.03° (as opposed to the 4.5° exemplary range of the converging beam in FIG. 1). Alternatively, larger or smaller slit widths may be used to trade off throughput against angular accuracy of the measurement. The position of slit 39 defines the incidence angle θ of the collimated beam on area 28. The inventors have found that setting θ=0.8° gives good results. Further alternatively, other types of collimators, such as a Göbel mirror, with or without a slit, may be used to collimate the incident X-ray beam for the diffuse reflectance measurement.

The same detector assembly 30 as was used to collect specularly-reflected radiation in the configuration of FIG. 1 is used to collect diffuse reflection in the configuration of FIG. 2. Thus, it can be seen that system 20 can be readily switched between the specular and diffuse measurement configurations. Due to the relative weakness of the diffuse reflections, it may be necessary to collect the X-rays over a longer integration time in the configuration of FIG. 2 than in that of FIG. 1.

Figure 3:
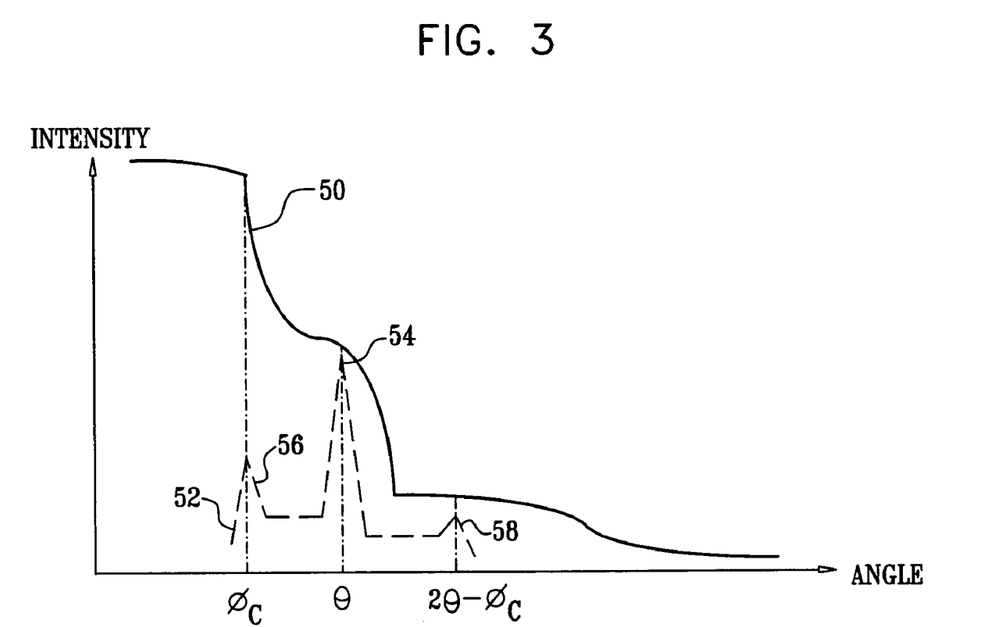
FIG. 3 is a schematic plot of specular and diffuse X-ray reflectance spectra that may be acquired using the system of FIGS. 1 and 2.

FIG. 3 is a schematic plot showing a specular reflection spectrum 50 and a diffuse reflection spectrum 52 captured by system 20, using the configurations shown in FIGS. 1 and 2, respectively. The spectra are plotted against the angle of reflection (or scattering) φ.

Spectrum 50 has a characteristic shoulder at the critical angle $\Phi_c$, and drops off in an oscillatory pattern with increasing angle. More detailed XRR spectra of this sort, with more pronounced, high-frequency oscillatory patterns, are shown, for example, in the above-mentioned U.S. Pat. Nos. 6,512,814 and 6,639,968. As explained in those patents, the location of the shoulder in spectrum 50 may be analyzed to determine the critical angle, and hence the density of the surface layer of sample 22, while the period and amplitude of the oscillations are indicative of the thickness and surface roughness of the surface layer of the sample. The greater the signal/background ratio of the XRR spectrum, the more accurately is processor 40 able to determine the surface layer characteristics. In some cases, the processor is also able to determine characteristics of underlying layers, beneath the sample surface. On the other hand, roughness of the sample surface decreases the amplitude of the oscillations in the XRR spectrum and increases the background due to diffuse reflections, so that it becomes more difficult to extract accurate measurements from spectrum 50.

Diffuse reflection spectrum 52 has a central peak 54 at the incidence angle θ of the collimated beam, and side peaks 56 and 58 corresponding to the Yoneda wings. Practically speaking, although both peaks 56 and 58 are generally seen in the classical tilt measurement set-up used by Yoneda, in the geometry of system 20 only peak 56 is actually seen by detector assembly 30. The single peak 56 is sufficient for the present purposes. Thus, assuming peaks 54 and 56 to be roughly Gaussian in shape, and ignoring peak 58, spectrum 52 can be modeled as follows:

$$R(\phi, \theta) = r\left(\frac{\theta + \phi}{2}\right)[G(\phi - \theta) + \alpha G(\phi - \Phi_C) + \gamma] \quad (1)$$

Here r is the measured specular reflectivity of sample 22 as a function of angle, and $$G(x) = \frac{1}{\sqrt{2\pi}\,\sigma} e^{-x^2/2\sigma^2},$$

wherein σ is the peak width characteristic. The coefficients α and γ respectively represent the amplitudes of peak 56 and the diffuse background between the peaks, relative to the specular peak at φ=θ. Typically, α is on the order of 0.01, while γ is on the order of 0.001.

The location of peak 56 gives an accurate reading of $\Phi_c$, which in many cases is more clearly defined than the shoulder of curve 50. The amplitude of peak 56 (in absolute terms or relative to peak 54) gives a measure of the roughness of the sample surface. The overall shape and amplitude of spectrum 52 are indicative of the diffuse reflection background appearing in spectrum 50. These features of spectrum 52 are used in conjunction with the features of spectrum 50 in determining surface layer characteristics of sample 22, using the method described below.

Figure 4:
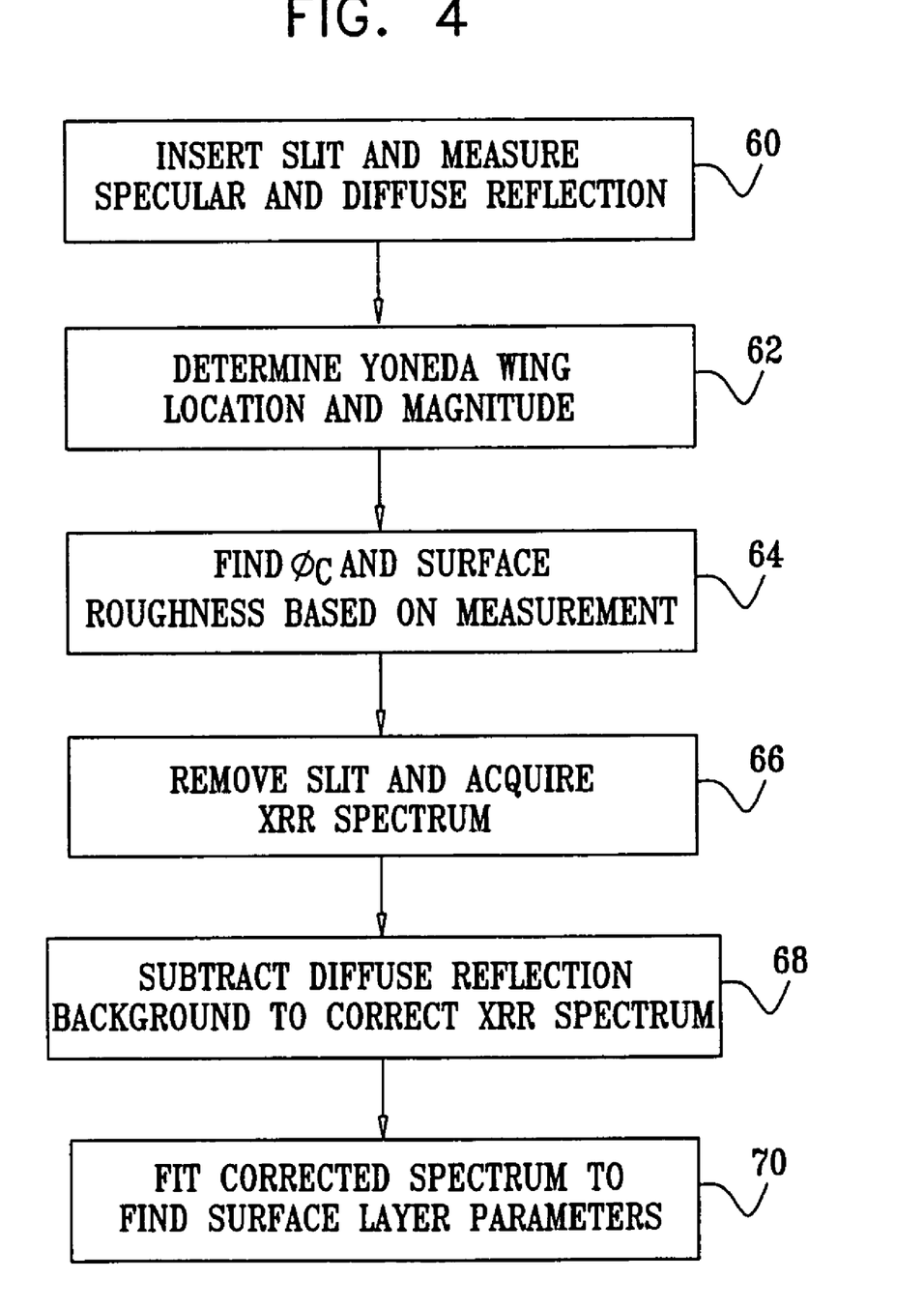
FIG. 4 is a flow chart that schematically illustrates a method for generating and analyzing X-ray reflectance spectra, in accordance with an embodiment of the present invention.

FIG. 4 is a flow chart that schematically illustrates a method for determining surface layer characteristics of sample 22, in accordance with an embodiment of the present invention. Although the steps of the method are listed hereinbelow in a certain order for the sake of conceptual clarity, it will be apparent to those skilled in the art that other orders of operations may be used to achieve the same purpose and are within the scope of the present invention.

To begin the method of FIG. 4, system 20 is configured as shown in FIG. 2, with slit 39 inserted in the beam path, in a diffuse reflection acquisition step 60. In this configuration, diffuse reflection spectrum 52 is acquired, including both specular peak 54 and Yoneda peak 56. Although FIG. 3 shows the diffuse reflection spectrum for only a single value of the incidence angle θ, multiple spectra may be acquired at different incidence angles in order to improve the accuracy of measurement and provide additional data points for modeling of the diffuse reflections. Processor 40 extracts selected features from spectrum 52, including the angular locations and magnitudes of peaks 54 and 56, at a peak measurement step 62. Alternatively or additionally, at step 60, slit 39 may be scanned continuously over a range of angles at a known pace, and the diffuse background radiation received by detector assembly 30 may be integrated over the entire range for use in background subtraction, as described below.

The processor uses the features of spectrum 52 in determining the critical angle and roughness of the surface layer of sample 22, at a surface modeling step 64. The roughness may be determined by mathematical modeling of the surface properties, as described in the above-mentioned article by Stömmer, for example. Alternatively, the relationship of Yoneda peak amplitude to roughness may be pre-calibrated by measuring diffuse reflections in system 20 from samples of materials of interest with known roughness characteristics. Further alternatively, spectrum 52 may be used in determining only the critical angle but not the surface roughness, or only the surface roughness but not the critical angle, or step 64 may be omitted, and the diffuse spectrum acquired at step 60 used only for the purpose of background subtraction, as described below.

Next, slit 39 is removed, and system 20 is operated in the configuration of FIG. 1 to acquire a specular XRR spectrum 50 using converging beam 27, at an XRR acquisition step 66. Optionally, the background due to the diffuse reflection contribution to the specular XRR measurement, based on the measurements made at step 60, is subtracted out of spectrum 50, at a background subtraction step 68. To estimate the total diffuse reflection background for any detection angle $\phi$, the diffuse reflection portion of equation (1), $$D(\phi, \theta) = r\left(\frac{\theta + \phi}{2}\right)[\alpha G(\phi - \Phi_C) + \gamma],$$

is integrated over the entire range of incident angles $\theta$ (above the critical angle) of the converging beam. The result is then subtracted from the measured reflection $r(\phi)$ to give a corrected specular reflection signal:

$$r'(\phi) = r(\phi) - \int_{\Phi_C}^{\max} D(\varphi, \theta) d\theta \quad (2)$$

Substituting in the actual parametric form of $D(\phi, \theta)$ and transforming to discrete coordinates (in terms of the pixels of detector array 32) gives the result:

$$r'[k] = r[k] - \left(\gamma + \frac{\alpha}{\sqrt{2\pi}\,\sigma}\exp\left(-\frac{(k-j_c)^2}{2\sigma^2}\right)\right)\sum_{j=j_c}^{\max} r[(k+j)/2] \quad (3)$$

wherein $j_c$ is the pixel coordinate of the critical angle. An equivalent result may be obtained by scanning slit 39 over the range of incidence angles at step 60, as described above, and then subtracting the integrated background thus obtained as a function of detection angle $\phi$ from the measured reflection $r(\phi)$.

Spectrum 50 (following background subtraction) is then compared to a theoretical model of the specular reflection in order to determine the characteristics of the surface layer of the sample, at a fitting step 70. Suitable fitting procedures are described, for example, in the above mentioned U.S. Pat. Nos. 6,512,814 and 6,639,968 and in U.S. Pat. No. 5,740,226. According to the theoretical model, the angular position of the initial shoulder in spectrum 50 and of peak 56 in spectrum 52 is determined by the density of the uppermost layer on the sample. The spatial frequency or frequencies of the fringes in spectrum 50 are indicative of the thickness of the film layers. The intensity of the higher-order fringes relative to the low-order ones is determined mainly by the roughness of the outer surface of the sample and, secondarily, of the interfaces between the film layers on the sample. The critical angle and surface roughness may also be ascertained on the basis of the location and amplitude of peak 56 in spectrum 52, as noted above.

Thus, upon completion of step 70, the physical properties of the outer layer on the sample—density, thickness, and outer surface roughness—are all known, on the basis of the information contained in spectra 50 and 52. In some cases, spectrum 50 can be further analyzed to determine the properties of one or more inner layers.

Figure 5:
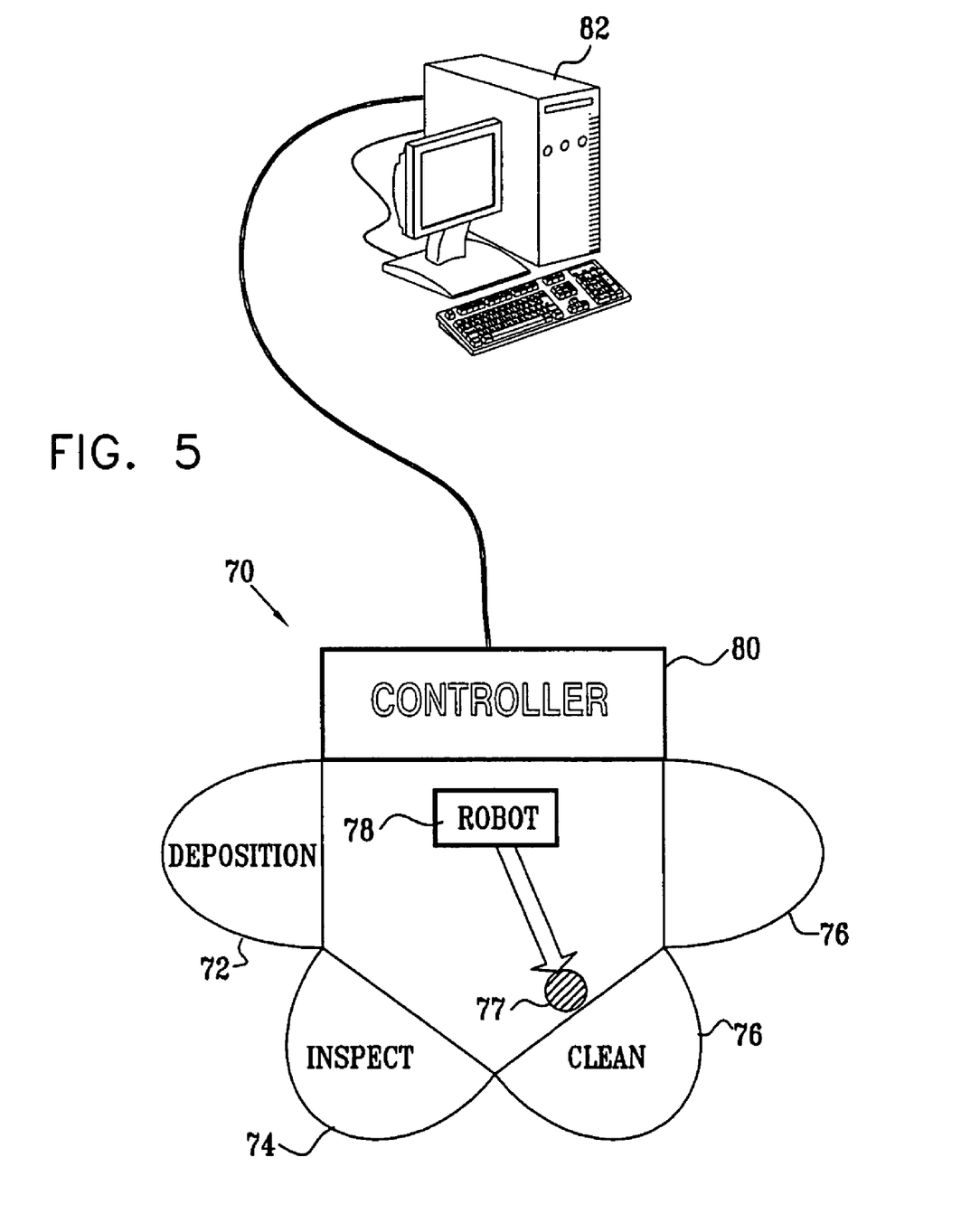
FIG. 5 is a schematic top view of a cluster tool for semiconductor device fabrication, including an inspection station in accordance with an embodiment of the present invention.

FIG. 5 is a schematic top view of a cluster tool 70 for use in semiconductor device fabrication, in accordance with an embodiment of the present invention. The cluster tool comprises multiple stations, including a deposition station 72, for depositing thin films on a semiconductor wafer 77, an inspection station 74, and other stations 76, as are known in the art, such as a cleaning station. Inspection station 74 is constructed and operates in a manner similar to system 20, as described hereinabove. A robot 78 transfers wafer 77 among stations 72, 74, 76, . . . , under the control of a system controller 80. Operation of tool 70 may be controlled and monitored by an operator using a workstation 82, coupled to controller 80.

Inspection station 74 is used to perform X-ray inspection of wafers by XRR, including specular or diffuse measurements, or both, before and after selected steps in production processes carried out by deposition station 72 and other stations in tool 70. In an exemplary embodiment, deposition station 72 is used to create thin films on wafer 77, and inspection station 74 performs XRR evaluation, as described above, by measuring the diffuse and specular reflectance characteristics of the wafer. This arrangement allows early detection of process deviations and convenient adjustment and evaluation of process parameters on production wafers, using controller 80 and possibly workstation 82.

Figure 6:
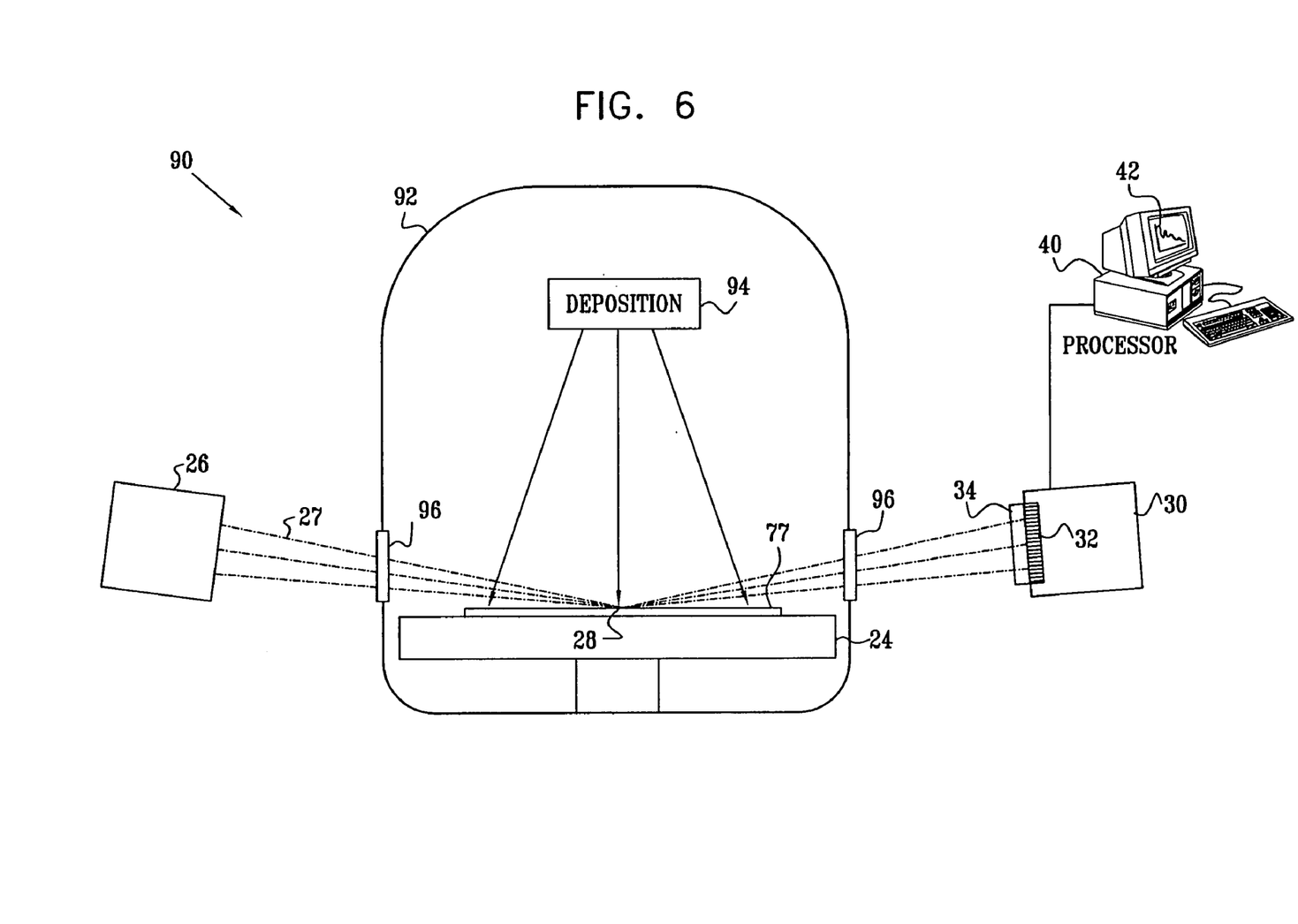
FIG. 6 is a schematic side view of a semiconductor processing chamber with X-ray inspection capability, in accordance with an embodiment of the present invention.

FIG. 6 is a schematic side view of a system 90 for semiconductor wafer fabrication and in situ inspection, in accordance with another embodiment of the present invention. System 90 comprises a vacuum chamber 92, containing deposition apparatus 94, for creating thin films on wafer 77, as is known in the art. The wafer is mounted on motion stage 24 within chamber 92. The chamber typically comprises X-ray windows 96, which may be of the type described in the above-mentioned Patent Application Publication U.S. Ser. No. 2001/0043668 A1. X-ray source 26 irradiates area 28 on wafer 77 via one of windows 96, in the manner described above. The shutter, knife edge and slit shown in FIG. 1 are omitted from FIG. 7 for the sake of simplicity, but typically, elements of this sort are integrated into source 26 or within chamber 92.

X-rays reflected from area 28 are received by array 32 in detector assembly 30 via another one of windows 96. Processor 40 receives signals from detector assembly 30, and processes the signals in order to assess characteristics of thin-film layers in production within chamber 92, by measuring the diffuse and/or specular reflectance characteristics of the wafer, as described above. The results of this assessment may be used in controlling deposition apparatus 94 so that the films produced by system 90 have desired characteristics, such as thickness, density and surface roughness.

Although the embodiments described above deal mainly with determining surface layer characteristics of semiconductor wafers, the principles of the present invention can similarly be used in other X-ray reflectometry applications, as well as in other types of radiation-based analysis, using not only X-rays, but also other ionizing radiation bands. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for inspection of a sample having a surface layer, the method comprising:
   acquiring a first reflectance spectrum of the sample while irradiating the sample with a collimated beam of X-rays;
   processing the first reflectance spectrum to measure a diffuse reflection property of the sample;
   acquiring a second reflectance spectrum of the sample while irradiating the sample with a converging beam of the X-rays; and
   analyzing the second reflectance spectrum using the diffuse reflection property so as to determine a characteristic of the surface layer of the sample.

2. The method according to claim 1, wherein acquiring the first reflectance spectrum comprises passing a converging beam through a slit so as to collimate the beam.

3. The method according to claim 1, wherein acquiring the first reflectance spectrum comprises irradiating the sample with the collimated beam at a predetermined incidence angle, and receiving the X-rays simultaneously over a range of elevation angles using a detector array.

4. The method according to claim 3, wherein acquiring the second reflectance spectrum comprises receiving the X-rays simultaneously over the range of elevation angles using the detector array that was also used in acquiring the first reflectance spectrum.

5. The method according to claim 1, wherein processing the first reflectance spectrum comprises detecting a Yoneda wing in the first reflectance spectrum.

6. The method according to claim 5, wherein detecting the Yoneda wing comprises determining a critical angle for total external reflection from the sample responsively to an angular location of the Yoneda wing.

7. The method according to claim 5, wherein detecting the Yoneda wing comprises determining a measure of roughness of the surface layer responsively to an amplitude of the Yoneda wing.

8. The method according to claim 1, wherein analyzing the second reflectance spectrum comprises estimating a diffuse reflection background responsively to the first reflectance spectrum, and subtracting the diffuse reflection background from the second reflectance spectrum.

9. The method according to claim 1, wherein analyzing the second reflectance spectrum comprises determining at least one of a density, a thickness and a surface roughness of the surface layer.

10. The method according to claim 1, wherein the sample comprises a semiconductor wafer, and wherein analyzing the second reflectance spectrum comprises determining a quality of a thin film layer formed on the wafer.

11. Apparatus for inspection of a sample having a surface layer, the apparatus comprising:
    a radiation source, which is adapted to direct a collimated beam of X-rays toward a surface of the sample in a first configuration of the apparatus, and to direct a converging beam of the X-rays toward the surface of the sample in a second configuration of the apparatus;
    a detector assembly, which is arranged to sense the X-rays reflected from the surface so as to generate first and second reflectance spectra as a function of elevation angle relative to the surface in the first and second configurations, respectively; and
    a signal processor, which is coupled to receive and process the first reflectance spectrum so as to measure a diffuse reflection property of the sample, and to analyze the second reflectance spectrum using the diffuse reflection property so as to determine a characteristic of the surface layer of the sample.

12. The apparatus according to claim 11, wherein the radiation source comprises an arrangement including a slit, which is introduced into a converging beam produced by the radiation source so as to collimate the beam in the first configuration.

13. The apparatus according to claim 11, wherein the detector assembly comprises a detector array, which is configured to receive the reflected X-rays simultaneously over a range of elevation angles in both the first and second configurations.

14. The apparatus according to claim 11, wherein the signal processor is adapted to process the first reflectance spectrum so as to detect a Yoneda wing in the first reflectance spectrum.

15. The apparatus according to claim 14, wherein the signal processor is adapted to determine a critical angle for total external reflection from the sample responsively to an angular location of the Yoneda wing.

16. The apparatus according to claim 14, wherein the signal processor is adapted to determine a measure of roughness of the surface layer responsively to an amplitude of the Yoneda wing.

17. The apparatus according to claim 11, wherein the signal processor is adapted to estimate a diffuse reflection background responsively to the first reflectance spectrum, and to subtract the diffuse reflection background from the second reflectance spectrum.

18. The apparatus according to claim 11, wherein the signal processor is adapted to analyze the second reflectance spectrum so as to determine at least one of a density, a thickness and a surface roughness of the surface layer.

19. The apparatus according to claim 11, wherein the sample comprises a semiconductor wafer, and wherein the signal processor is adapted to analyze the second reflectance spectrum comprises so as to determine a quality of a thin film layer formed on the wafer.

20. A cluster tool for producing microelectronic devices, comprising:
    a deposition station, which is adapted to deposit a thin-film layer on a surface of a semiconductor wafer; and
    an inspection station, comprising:
       a radiation source, which is adapted to direct a collimated beam of X-rays toward the surface of the wafer in a first configuration of the inspection station, and to direct a converging beam of the X-rays toward the surface of the wafer in a second configuration of the inspection station;
       a detector assembly, which is arranged to sense the X-rays reflected from the surface so as to generate first and second reflectance spectra as a function of elevation angle relative to the surface in the first and second configurations, respectively; and a signal processor, which is coupled to receive and process the first reflectance spectrum so as to measure a diffuse reflection property of the surface, and to analyze the second reflectance spectrum using the diffuse reflection property so as to determine a characteristic of the thin-film layer.

21. Apparatus for producing microelectronic devices, comprising:

a production chamber, which is adapted to receive a semiconductor wafer;

a deposition device, which is adapted to deposit a thin-film layer on a surface of the semiconductor wafer within the chamber;

a radiation source, which is adapted to direct a collimated beam of X-rays toward the surface of the wafer in the production chamber in a first configuration of the source, and to direct a converging beam of the X-rays toward the surface of the wafer in the production chamber in a second configuration of the source;

a detector assembly, which is arranged to sense the X-rays reflected from the surface of the wafer in the production chamber so as to generate first and second reflectance spectra as a function of elevation angle relative to the surface in the first and second configurations, respectively; and a signal processor, which is coupled to receive and process the first reflectance spectrum so as to measure a diffuse reflection property of the surface, and to analyze the second reflectance spectrum using the diffuse reflection property so as to determine a characteristic of the thin-film layer.

* * * * *